United States Patent [19]

Draber et al.

[11] Patent Number: 5,334,610
[45] Date of Patent: Aug. 2, 1994

[54] α-ARYL-α-HYDROXY-β-IMIDAZOLINYL-PROPIONAMIDES

[75] Inventors: Wilfried Draber; Hilmar Bischoff, both of Wuppertal, Fed. Rep. of Germany

[73] Assignee: Bayer Aktiengesellschaft, Leverkusen, Fed. Rep. of Germany

[21] Appl. No.: 4,341

[22] Filed: Jan. 14, 1993

[30] Foreign Application Priority Data

Jan. 23, 1992 [DE]  Fed. Rep. of Germany ....... 4201709

[51] Int. Cl.$^5$ ................ A61K 31/415; C07D 233/06
[52] U.S. Cl. ............................... 514/401; 548/349.1; 548/300.7
[58] Field of Search ................ 548/349.1, 300.7; 514/401

[56] References Cited

U.S. PATENT DOCUMENTS 4,136,188  1/1979  Ishikawa et al. ............... 424/273 R
4,226,876  10/1980  Copp et al. ..................... 548/349.1
4,284,584  8/1981  Findeisen ....................... 260/545 R

FOREIGN PATENT DOCUMENTS 9100862  1/1991  PCT Int'l Appl. .

OTHER PUBLICATIONS

Hawkins, et al., J. Am. Chem. Soc. 71, 1949, pp. 2530–2531.
Ozawa, et al., J. Am. Chem. Soc. 107, 1985, pp. 3235–3245.
Roedig, et al., Tetrahedron vol. 33, 1977, pp. 2437–2440.
Kolasa, et al., J. Org. Chem., 1987, 52, pp. 4978–4984.

*Primary Examiner*—Patricia L. Morris
*Attorney, Agent, or Firm*—Sprung Horn Kramer & Woods

[57] ABSTRACT

The present invention relates to novel α-aryl-α-hydroxy-β-imidazolinyl-propionamides of the general formula (I)

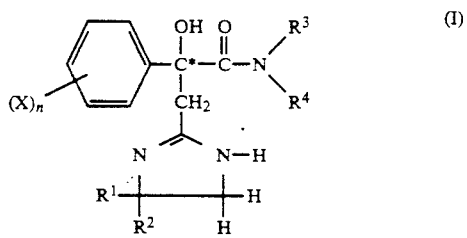

in which n, $R^1$ to $R^4$ and X have the meaning indicated in the description, to a process for their preparation and to their use in medicaments.

5 Claims, No Drawings

α-ARYL-α-HYDROXY-β-IMIDAZOLINYL-PROPIONAMIDES

The present invention relates to novel α-aryl-α-hydroxy-β-imidazolinyl-propionamides, to a process for their preparation and to their use in medicaments.

The novel compounds according to the invention are characterised by the following general formula (I)

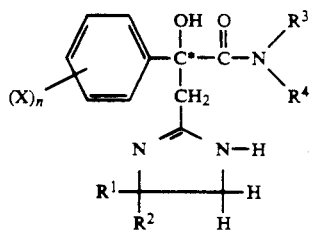

in which
n represents the numbers 0 or 1 to 5,
$R^1$ and $R^2$ are the same or different and represent individually hydrogen or alkyl or represent together alkanediyl (alkylene),
$R^3$ represents hydrogen or alkyl,
$R^4$ represents hydrogen or in each case optionally substituted alkyl, cycloalkyl, cycloalkylalkyl, aryl or arylalkyl, or
$R^3$ and $R^4$ form, together with the nitrogen atom to which they are bound, an optionally substituted, saturated or unsaturated nitrogen heterocycle, which optionally contains further hereto atoms such as oxygen or nitrogen, and
X represents halogen, or alkyl or alkoxy each of which is optionally substituted with halogen.

Alkyl, also in compounds with hereto atoms, such as, for example, in alkoxy, is in each case straight-chain or branched.

The invention also relates to physiologically tolerated acid adducts of the compounds of the formula (I).

The present invention preferably relates to compounds of the formula (I), in which
n represents the numbers 0, 1, 2 or 3,
$R^1$ and $R^2$ are the same or different and represent individually hydrogen or $C_1-C_6$-alkyl or represent together $C_1-C_6$-alkanediyl,
$R^3$ represents hydrogen or $C_1-C_6$-alkyl,
$R^4$ represents hydrogen, $C_1-C_6$-alkyl, which is optionally substituted with fluorine, chlorine or $C_1-C_4$-alkoxy, $C_3-C_7$-cycloalkyl or $C_3-C_7$-cycloalkyl-$C_1-C_4$-alkyl each of which is optionally substituted with fluorine, chlorine, bromine or $C_1-C_4$-alkyl, in each case optionally substituted phenyl, naphthyl, phenyl-$C_1-C_4$-alkyl or naphthyl-$C_1-C_4$-alkyl (the possible substituents preferably being chosen from one of the following: fluorine, chlorine, bromine, cyano, nitro, or $C_4-C_4$-alkyl, $C_1-C_4$-alkoxy, $C_1-C_4$-alkylthio, $C_1-C_4$-alkylsulphinyl or $C_1-C_4$-alkylsulphonyl each of which is optionally substituted with fluorine and/or chlorine), or
$R^3$ and $R^4$ form, together with the nitrogen atom to which they are bound, a saturated or unsaturated, five- to seven-membered nitrogen heterocycle, which is optionally substituted once to three times with $C_1-C_4$-alkyl and which optionally contains a further hetero atom such as oxygen or nitrogen, and
X represents fluorine, chlorine, bromine, or $C_1-C_4$-alkyl or $C_1-C_4$-alkoxy each of which is optionally substituted with fluorine and/or chlorine.

In particular the present invention relates to compounds of the formula (I), in which
n represents the numbers 0, 1 or 2,
$R^1$ and $R^2$ are the same or different and represent individually hydrogen, methyl, ethyl, propyl, isopropyl, butyl, isobutyl or sec-butyl or represent together butane-1,4-diyl (tetramethylene) or pentane-1,5-diyl (pentamethylene),
$R^3$ represents hydrogen, methyl, ethyl, propyl, isopropyl, butyl, isobutyl or sec-butyl,
$R^4$ represents hydrogen, methyl, ethyl, propyl, isopropyl, butyl, isobutyl, sec-butyl, tert-butyl, pentyl, isopentyl, sec-pentyl, tert-pentyl, hexyl, cyclopentyl, cyclohexyl, cyclopentyl methyl, cyclohexylmethyl, at any one time optionally substituted phenyl, benzyl or phenylethyl (the possible substituents in particular being chosen from the following: fluorine, chlorine, methyl, ethyl, trifluoromethyl, methoxy, ethoxy, difluoromethoxy, trifluoromethoxy), or
$R^3$ and $R^4$ represent, together with the nitrogen atom to which they are bound, pyrrolidinyl, piperidinyl, morpholinyl or piperazinyl, each of which is optionally substituted once to three times with methyl and/or ethyl, and
X represents fluorine, chlorine, methyl, ethyl, trifluoromethyl, methoxy, ethoxy, difluoromethoxy or trifluoromethoxy.

The compounds of the formula (I) possess at least one asymmetrically substituted carbon atom (marked with *) and can therefore occur in various stereoisomeric forms. The invention relates to the individual possible stereoisomers as well as to the various possible mixtures of these stereoisomers.

Preferred compounds according to the invention are also addition products composed of acids and those compounds of the formula (I) in which n, $R^1$, $R^2$, $R^3$, $R^4$ and X have those meanings, which have already been indicated as preferred for the index and the substituents in connection with the description of the compounds according to the invention.

The acids which can be added include preferably hydrohalic acids such as, for example, hydrochloric acid and hydrobromic acid, additionally phosphoric acid, acetic acid, formic acid, maleic acid, tartaric acid, citric acid, oxalic acid, salicylic acid, sorbic acid, lactic acid, sulphuric acid, methanesulphonic acid and p-toluenesulphonic acid.

The compounds of the formula (I) according to the invention are obtained if methylimidazolines of the general formula (II)

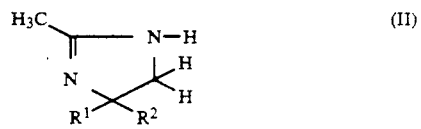

in which
$R^1$ and $R^2$ have the abovementioned meaning,
are reacted with phenylglyoxylamides of the general formula (III)

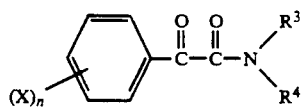

in which n, $R^3$, $R^4$ and X have the abovementioned meaning, optionally in the presence of a diluent and optionally in the presence of a basic catalyst.

If, for example, 2-methyl-4-propyl-2-imidazoline and phenylglyoxylic acid dimethylamide are used as starting materials in the process according to the invention for the preparation of the compounds of the formula (i), then the course of the reaction can be indicated by the following formula diagram:

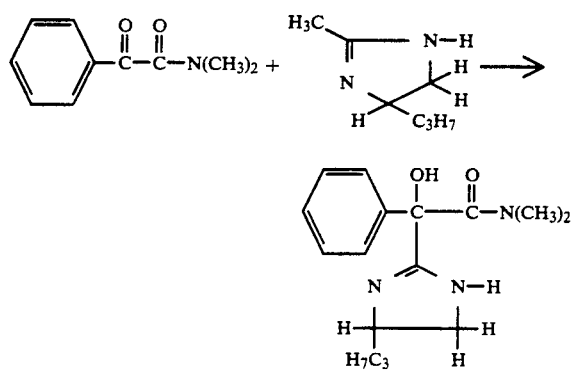

The methylimidazolines which are to be used as starting materials in the process according to the invention for the preparation of compounds of the formula (I) are defined generally by the formula (II).

In formula (II) $R^1$ and $R^2$ have preferably or in particular those meanings which have already been indicated above in connection with the description of the compounds according to the invention of the formula (I) as being preferable or particularly preferred for $R^1$ and $R^2$.

The starting materials of the formula (II) are known and/or can be prepared according to processes that are known per se (cf. J. Am. Chem. Soc. 71 (1949), 2530–2531).

The phenylglyoxylamides which are additionally to be used as starting materials in the process according to the invention are defined generally by the formula (III).

In formula (III) n, $R^3$, $R^4$ and X have preferably or in particular those meanings which have already been indicated above in connection with the description of the compounds according to the invention of the formula (I) as being preferable or particularly preferred for n, $R^3$, $R^4$ and X.

The starting materials of the formula (III) are known and/or can be prepared according to processes which are known per se (cf. DE-OS (German Published Specification) 2614240; EP-A 53408; J. Am. Chem. Soc. 107 (1985), 3235–3245; Tetrahedron 33 (1977), 2437–2440; J. Org. Chem. 52 (1987), 4978–4984; Preparation Examples).

The process according to the invention for the preparation of the novel compounds of the formula (I) is preferably carried out using diluents. In this connection practically all inert organic solvents may be considered as possible diluents. These include preferably aliphatic and aromatic, optionally halogenated, hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether, methyl tert-butyl ether, dipropyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone as well as dimethyl sulphoxide, tetramethylene sulphone and hexamethylphosphoric acid triamide.

The preparative process according to the invention is preferably carried out using a basic catalyst. Preferably organic, basic nitrogen compounds come into consideration as catalysts. As examples of these there may be mentioned: trimethylamine, triethylamine, diisopropylamine, diisobutylamine, dicyclohexylamine, ethyldiisopropylamine, N,N-dimethyl-benzylamine, pyridine, 4-dimethylaminopyridine, pyrrolidine, piperidine and 4-methylpiperidine.

The reaction temperatures in the process according to the invention can be varied over a wide range. In general the temperatures are between 0° C. and 150° C., preferably temperatures between 10° C. and 100° C.

The process according to the invention is generally carried out under atmospheric pressure. It is however also possible to work under elevated or reduced pressure.

For carrying out the process according to the invention the starting materials required in each case are generally employed in approximately equimolar quantities. It is however also possible to use one of the two components employed in each case in a relatively large excess. The reactions are generally carried out in a suitable diluent in the presence of a basic catalyst, and the reaction mixture is stirred for several hours at the temperature required in each case. Working up is effected in the process according to the invention in each case by means of customary methods (cf. the preparation examples).

The compounds according to the invention of the general formula (I) show a valuable pharmacological spectrum of activity.

While having only a small effect on the circulation they lower blood sugar and can therefore be used for the treatment of diabetes.

The compounds according to the invention can be converted in a known manner into the customary formulations, such as tablets, capsules, coated tablets, pills, granules, aerosols, syrups, emulsions, suspensions and solutions, using inert, non-toxic, pharmaceutically suitable excipients or solvents. The therapeutically active compound should in each case be present in a concentration of about 0.5 to 90% by weight of the total mixture, that is to say in amounts which suffice to achieve the dosage range indicated.

Administration is effected in the customary manner, preferably orally or parenterally, in particular perlingually or intravenously.

In general, it has proved advantageous in the case of oral administration to administer amounts of about 0.01 to 200 mg/kg, preferably 0.1 to 50 mg/kg of body weight to achieve effective results.

Nevertheless, it can at times be necessary to deviate from the amounts mentioned, and in particular to do so as a function of the body weight of the experimental animal (in tests on an animal model) or of the nature of the administration route, but also because of the species of animal and its individual behaviour towards the medicament or the nature of the formulation thereof and the time or interval over which administration takes place. Thus it can suffice in some cases to manage with less than the abovementioned minimum amount, whilst in other cases the upper limit mentioned must be exceeded. Where relatively large amounts are administered, it can be advisable to divide these into several individual administrations over the course of the day. The same dosage range is envisaged for administration in human medicine. In this connection the above statements apply similarly.

Preparation Examples

EXAMPLE 1

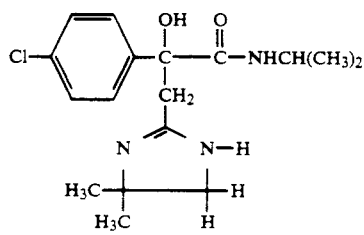

A solution of 11.2 g (0.10 mol) of 2,4,4-trimethyl-2-imidazoline in 60 ml of diethyl ether/methylene chloride (5:1 by vol.) is added at dropwise with stirring at 20° C. to a mixture of 22.55 g (0.10 mol) of (4-chlorophenyl)glyoxylic acid isopropylamide, 200 ml of diethyl ether and 0.2 g of piperidine. The reaction mixture is heated under reflux for 2 hours with stirring and subsequently concentrated. The residue is obtained in a crystalline form from methyl tert-butyl ether and is isolated by filtering with suction.

26.9 g (80% of theory) of 2-(4-chloro-phenyl)-2-hydroxy-3-(4,4-dimethyl-2-imidazolinyl)-propanoic acid isopropylamide is obtained with a melting point of 118° C.

In an analogous fashion to Example 1, and corresponding to the general description of the preparation process according to the invention, the compounds of the formula (I) listed in the following Table 1 can for example also be prepared.

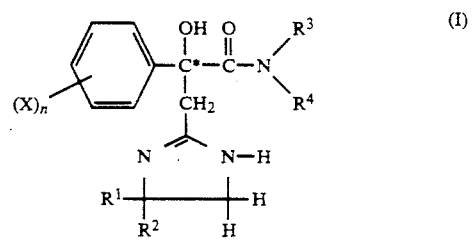

TABLE 1

Examples of the compounds of the formula (I)

| Ex. No. | n | $R^1$ | $R^2$ | $R^3$ | $R^4$ | (Position) X | Melting point (°C.) |
|---|---|---|---|---|---|---|---|
| 2 | 0 | $CH_3$ | $CH(CH_3)_2$ | H | $CH(CH_3)_2$ | — | 122 |
| 3 | 1 | $CH_3$ | $CH_3$ | H | $CH(CH_3)_2$ | (4-)F | 124 |
| 4 | 0 | $CH_3$ | $CH(CH_3)_2$ | H | $CH_3$ | — | 108 |
| 5 | 1 | $C_2H_5$ | $C_2H_5$ | H | $CH(CH_3)_2$ | (4-)Cl | 99 |
| 6 | 1 | $CH_3$ | $CH(CH_3)_2$ | H | $CH(CH_3)_2$ | (4-)F | 95 |
| 7 | 1 | $CH_3$ | $CH(CH_3)_2$ | H | $CH(CH_3)_2$ | (4-)Cl | 88 |
| 8 | 1 | $CH_3$ | $C_2H_5$ | H | $CH(CH_3)_2$ | (4-)Cl | 114 |
| 9 | 1 | —$(CH_2)_5$— | | H | $CH(CH_3)_2$ | (4-)F | 103 |
| 10 | 1 | —$(CH_2)_5$— | | H | $CH(CH_3)_2$ | (4-)Cl | 100 |
| 11 | 1 | $CH_3$ | $CH(CH_3)_2$ | H | H | (2-)Cl | 105 |
| 12 | 1 | $CH_3$ | $CH_2CH(CH_3)_2$ | H | H | (2-)Cl | 115 |
| 13 | 1 | $CH_3$ | $CH_2CH(CH_3)_2$ | H | H | (4-)F | 116 |
| 14 | 0 | $CH_3$ | $CH_2CH(CH_3)_2$ | H | $CH(CH_3)_2$ | — | 81 |
| 15 | 0 | $CH_3$ | $CH(CH_3)_2$ | H | $CH(CH_3)_2$ | — | 103 |
| 16 | 1 | —$(CH_2)_5$— | | H | H | (4-)F | 139 |
| 17 | 2 | $CH_3$ | $CH(CH_3)_2$ | H | H | (2,4-)Cl | 110 |
| 18 | 1 | —$(CH_2)_5$— | | H | H | (3-)Cl | 162 |
| 19 | 1 | —$(CH_2)_5$— | | H | H | (3-)OCF$_3$ | 129 |
| 20 | 1 | $C_2H_5$ | $C_2H_5$ | H | H | (4-)Cl | 123 |
| 21 | 2 | $CH_3$ | $CH(CH_3)_2$ | H | H | (3-)Cl,(4-)OCF$_3$ | 111 |
| 22 | 0 | $CH_3$ | $CH(CH_3)_2$ | H | $C(CH_3)_3$ | — | (oil) |
| 23 | 1 | $C_2H_5$ | $C_2H_5$ | H | H | (4-)F | 115 |
| 24 | 1 | $CH_3$ | $CH(CH_3)_2$ | H | H | (2-)OCF$_3$ | 125 |
| 25 | 1 | $CH_3$ | $CH(CH_3)_2$ | H | H | (3-)Cl | 122 |
| 26 | 1 | —$(CH_2)_5$— | | H | H | (2-)OCF$_3$ | 115 |
| 27 | 0 | —$(CH_2)_4$— | | H | H | — | 114 |
| 28 | 2 | $CH_3$ | $CH(CH_3)_2$ | H | H | (3,4-)Cl | 129 |
| 29 | 1 | $CH_3$ | $CH(CH_3)_2$ | H | H | (3-)OCF$_3$ | 110 |
| 30 | 1 | H | $CH_3$ | H | H | (4-)F | 123 |
| 31 | 2 | H | $CH_3$ | H | H | (3,4-)Cl | 129 |
| 32 | 1 | —$(CH_2)_5$— | | H | H | (4-)Cl | 196 |
| 33 | 0 | $CH_3$ | $CH_3$ | H | $CH(CH_3)_2$ | — | 111 |
| 34 | 0 | —$(CH_2)_5$— | | H | H | — | 139 |
| 35 | 0 | —$(CH_2)_5$— | | H | $CH(CH_3)_2$ | — | 143 |
| 36 | 0 | H | $CH_3$ | H | $CH(CH_3)_2$ | — | 102 |
| 37 | 1 | H | $CH_2CH(CH_3)_2$ | H | H | (4-)Cl | 130 |
| 38 | 1 | $CH_3$ | $CH(CH_3)_2$ | H | H | (3-)F | 123 |
| 39 | 1 | H | $CH_3$ | H | H | (4-)Cl | 136 |
| 40 | 1 | H | $CH_3$ | H | H | (4-)OCF$_3$ | 108 |

TABLE 1-continued

Examples of the compounds of the formula (I)

| Ex. No. | n | R¹ | R² | R³ | R⁴ | (Position) X | Melting point (°C.) |
|---|---|---|---|---|---|---|---|
| 41 | 1 | CH₃ | CH(CH₃)₂ | H | H | (3-)OCH₃ | 103 |
| 42 | 1 | CH₃ | CH(CH₃)₂ | H | H | (3-)CH₃ | 116 |
| 43 | 1 | H | CH₃ | H | H | (3-)OCH₃ | 120 |
| 44 | 1 | H | CH₃ | H | H | (3-)CH₃ | 105 |
| 45 | 1 | CH₃ | CH(CH₃)₂ | H | H | (4-)F | 121 |
| 46 | 1 | H | CH₃ | H | H | (3-)F | 124 |
| 47 | 2 | H | CH₃ | H | H | (3-)Cl,(4-)OCF₃ | 112 |
| 48 | 0 | H | CH₃ | H | H | — | 102 |
| 49 | 0 | H | CH₂CH(CH₃)₂ | H | H | — | 121 |
| 50 | 0 | CH₃ | CH(CH₃)₂ | H | H | — | 124 |
| 51 | 1 | CH₃ | CH(CH₃)₂ | H | H | (4-)Cl | 138 |
| 52 | 1 | CH₃ | CH₃ | H | H | (4-)Cl | 123 |
| 53 | 1 | H | H | H | H | (4-)Cl | 146 |
| 54 | 1 | H | H | H | H | (4-)OCF₃ | 139 |
| 55 | 1 | CH₃ | CH₃ | H | H | (4-)F | 128 |
| 56 | 1 | CH₃ | CH(CH₃)₂ | H | H | (4-)OCF₃ | 118 |
| 57 | 1 | H | H | H | H | (3-)F | 150 |
| 58 | 1 | —(CH₂)₅— | | H | H | (3-)OCF₃ | 177*⁾ |
| 59 | 1 | —(CH₂)₄— | | H | H | (4-)Cl | 139 |
| 60 | 1 | CH₃ | C₂H₅ | H | H | (4-)F | 103 |
| 61 | 0 | C₂H₅ | C₂H₅ | H | CH(CH₃)₂ | — | 79 |
| 62 | 2 | —(CH₂)₅— | | H | H | (2,4-)Cl | 116 |
| 63 | 1 | CH₃ | C₂H₅ | H | H | (4-)Cl | 112 |
| 64 | 0 | —(CH₂)₅— | | H | C(CH₃)₃ | — | 106 |
| 65 | 0 | CH₃ | CH₃ | H | C(CH₃)₃ | — | 103 |
| 66 | 0 | CH₃ | CH₃ | H | 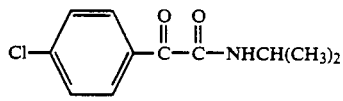 | — | 121 |
| 67 | 1 | CH₃ | CH₃ | H | C(CH₃)₃ | (4-)Cl | 125-126 |
| 68 | 1 | CH₃ | CH₃ | H | C(CH₃)₃ | (4-)F | 104 |

*⁾HCl adduct

STARTING MATERIALS OF THE FORMULA (III)

EXAMPLE (III-1)

Cl—⟨C₆H₄⟩—C(=O)—C(=O)—NHCH(CH₃)₂

A solution of 6.9 g (117 mmol) of isopropylamine in 50 ml of methyl tert-butyl ether is added dropwise at 20° C. with stirring to a mixture of 23.3 g (117 retool) of methyl (4-chloro-phenyl)-glyoxylate and 200 ml of methyl tert-butyl ether. The reaction mixture is stirred for 20 hours at 20° C. and then concentrated under water pump vacuum and subsequently degassed under oil pump vacuum.

21.3 g (81% of theory) of (4-chloro-phenyl)-glyoxylic acid isopropylamide are obtained with a melting point of 79° C.

APPLICATION EXAMPLES

The blood glucose-lowering effect of the substances to be investigated was tested in male Wistar rats with a weight between 140 and 190 g. For this purpose, the rats were weighed 18 h before the administration of the substances, divided into groups of 6 animals and fasted. The substances to be investigated were suspended, directly before administration, in aqueous 0.75% tragacanth suspension with an Ultra-Turrax. Administration of the tragacanth suspension (control animals) or the substances suspended in tragacanth was effected by garage.

Removal of blood from the retro-orbital venous plexus was effected in each rat at 30, 60, 120 and 240 min. after administration. On each occasion 30 μl of blood were removed with an automatic dilutor and deproteinised with 0.3 ml of uranyl acetate (0.16%). After centrifugation the glucose in the supernatant was determined photometrically by the glucose oxidase method using 4-aminophenazone as the colour reagent in an EPOS Analyzer 5060. Evaluation of the results was effected with Student's t test after previous examination for homogeneity of the variances, with $p<0.05$ being chosen as the limit of significance.

Substances which produced a significant reduction of at least 10% in the blood glucose concentration of rats at one time point, when compared to the control group which only received tragacanth suspension, have been indicated as effective.

The following Table A contains the changes that were found in blood glucose concentration expressed as per cent of the control.

TABLE A

| Compound from Preparation Example No. | Decrease of the blood glucose concentrations in % of the control 30 mg/kg p.o. |
|---|---|
| 1 | 38 |
| 10 | 17 |
| 3 | 39 |
| 20 | 26 |
| 22 | 26 |
| 23 | 24 |
| 24 | 13 |
| 25 | 19 |

TABLE A-continued

| Compound from Preparation Example No. | Decrease of the blood glucose concentrations in % of the control 30 mg/kg p.o. |
|---|---|
| 33 | 23 |
| 34 | 17 |
| 35 | 28 |
| 36 | 18 |
| 45 | 21 |
| 51 | 21 |
| 52 | 22 |
| 65 | 27 |
| 67 | 42 |
| 68 | 43 |

We claim:

1. A compound of the formula

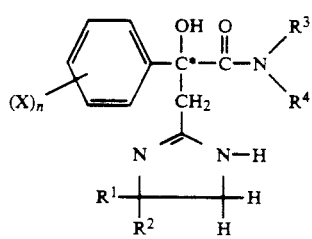

in which n is a number from 0 to 5, $R^1$ and $R^2$ each independently is hydrogen or $C_1$-$C_6$-alkyl or together are $C_4$-$C_6$-alkanediyl, $R^3$ is hydrogen or $C_1$-$C_6$-alkyl, $R^4$ represents hydrogen; $C_{1-6}$-alkyl optionally substituted by fluorine, chlorine, or $C_{1-4}$-alkoxy; $C_{3-7}$-cycloalkyl or $C_{3-7}$-cycloalkyl-$C_{1-4}$-alkyl each optionally substituted by fluorine, chlorine, bromine or $C_{1-4}$alkyl; phenyl, naphthyl, phenyl-$C_{1-4}$-alkyl or naphthyl-$C_{1-4}$-alkyl each optionally substituted by fluorine, chlorine, bromine, cyano or nitro or by $C_{1-4}$alkyl, $C_{1-4}$-alkoxy, $C_{1-4}$-alkylthio, $C_{1-4}$-alkylsulphinyl or $C_{1-4}$-alkylsulphonyl each optionally substituted by fluorine and/or chlorine;

X represents halogen, or $C_1$-$C_4$-alkyl or $C_1$-$C_4$-alkoxy each of which is optionally substituted by fluorine and/or chlorine, or a physiologically tolerated acid adduct thereof.

2. A compound or adduct thereof according to claim 1, in which n is a number from 0 to 3, $R^1$ and $R^2$ each independently is hydrogen, methyl, ethyl, propyl, isopropyl, butyl, isobutyl or sec-butyl, or together are butane-1,4-diyl (tetramethylene) or pentane-1,5-diyl (pentamethylene), $R^3$ is hydrogen, methyl, ethyl, propyl, isopropyl, butyl, isobutyl, or sec-butyl, $R^4$ represents hydrogen, methyl, ethyl, propyl, isopropyl, butyl, isobutyl, sec-butyl, tert-butyl, pentyl, isopentyl, sec-pentyl, tert-pentyl, hexyl, cyclopentyl, cyclohexyl, cyclopentylmethyl, cyclohexylmethyl, or phenyl, benzyl or phenylethyl each of which is optionally substituted by a member selected from the group consisting of fluorine, chlorine, methyl, ethyl, trifluoromethyl, methoxy, ethoxy, difluoromethoxy and trifluoromethoxy, and X represents fluorine, chlorine, bromine, methyl, ethyl, trifluoromethyl, methoxy, ethoxy, difluoromethoxy or trifluoromethoxy.

3. A blood sugar-lowering composition comprising a compound or adduct thereof according to claim 1 and a physiologically tolerated diluent.

4. A method of lowering the sugar content of a patient's blood which comprises administering to such patient a blood sugar-lowering effective amount of a compound or adduct thereof according to claim 1.

5. A compound according to claim 1, wherein such compound is selected from the group consisting of

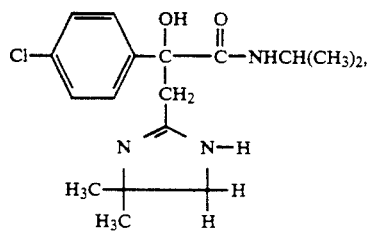

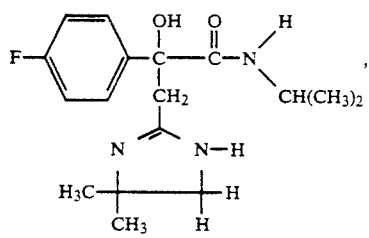

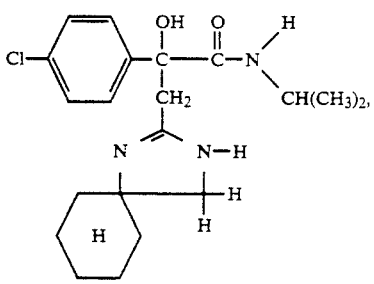

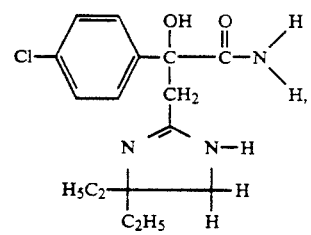

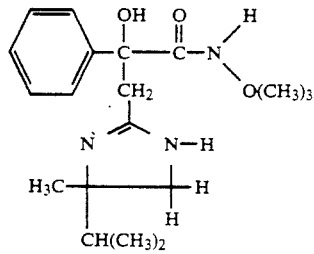

-continued
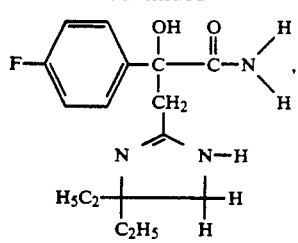
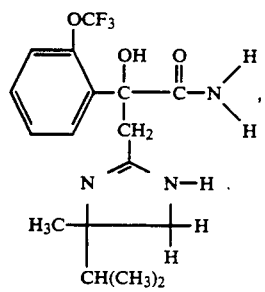
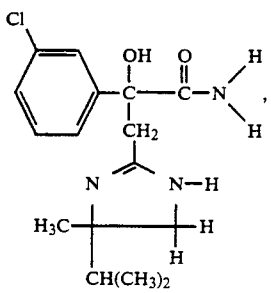
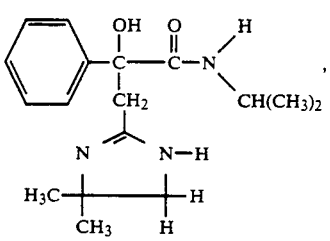
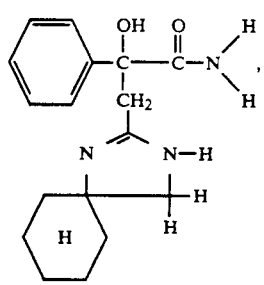
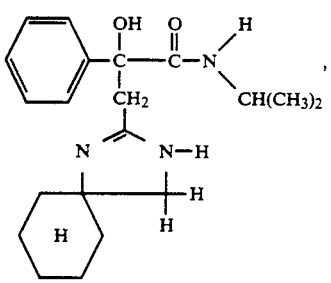
-continued
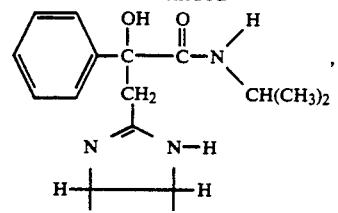
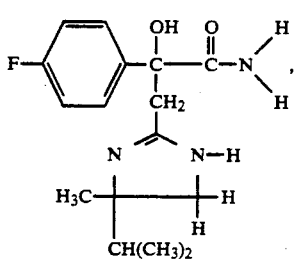
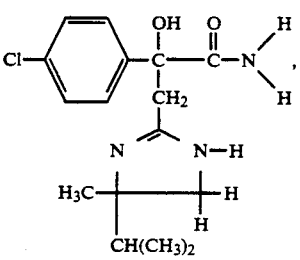
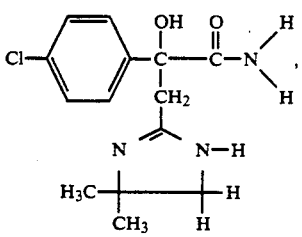
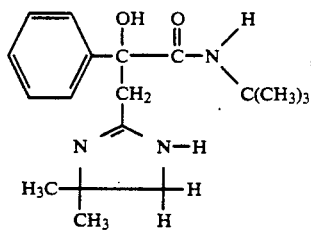
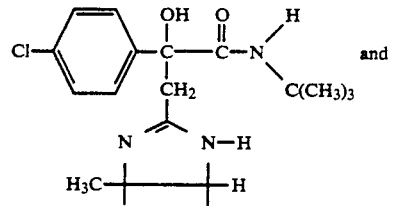
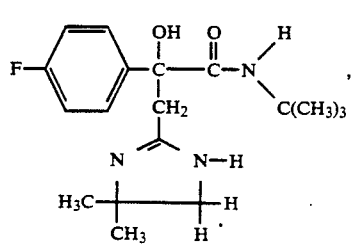
or a physiologically tolerated acid adduct thereof.
* * * * *